United States Patent [19]

Pazoles et al.

[11] Patent Number: 5,759,995
[45] Date of Patent: Jun. 2, 1998

[54] ANTIVIRAL TREATMENT

[75] Inventors: Christopher J. Pazoles; Scott A. Siegel, both of Westborough, Mass.

[73] Assignee: Phytera, Inc., Worcester, Mass.

[21] Appl. No.: 711,412

[22] Filed: Sep. 5, 1996

[51] Int. Cl.⁶ .................................................. A61K 38/00
[52] U.S. Cl. ........................... 514/9; 530/317; 530/329; 514/16
[58] Field of Search ............................ 514/11, 16, 9; 530/317, 329

[56] References Cited

U.S. PATENT DOCUMENTS 5,444,043  8/1995  Fenical et al. .......................... 514/9

*Primary Examiner*—Cecilia J. Tsang
*Assistant Examiner*—S. G. Marshall
*Attorney, Agent, or Firm*—Clark & Elbing LLP

[57] ABSTRACT

A method of inhibiting viral infection with a pharmaceutical composition containing cyclomarin-A.

14 Claims, No Drawings

ANTIVIRAL TREATMENT

BACKGROUND OF THE INVENTION

The invention relates to peptide-based antiviral compositions.

Numerous diseases and conditions are induced or exacerbated by viruses including hepatitis A, hepatitis B, and hepatitis C; influenza and parainfluenza III; respiratory syncytial virus; human papilloma virus; rhino virus; adenovirus; HIV; Coxsackie virus; echo virus; and the herpesvirus family.

The herpesvirus family includes Herpes Simplex virus 1 (HSV-1), Herpes Simplex virus 2 (HSV-2), Cytomegalovirus (CMV), Varicella Zoster virus (VZV), Epstein-Barr virus (EPV), and Human Herpes virus 6–8 (HHV-6, HHV-7, and HHV-8). Specific herpes-associated medical conditions include HSV-induced keratitis, conjunctivitis, blepharitis, keratoconjunctivitis, CMV retinitis, CMV gastritis, systemic and ocular CMV infection, primary and recurrent genital herpes, primary and recurrent oral herpes, herpes encephalitis, neonatal herpes, and herpes zoster infections including chickenpox and shingles.

Herpes infections can be symptomatic or asymptomatic, and can be recurrent. Symptoms include pain, fever, itching, inflammation, chills, headache, bizarre behavior, hallucinations, aphasia, and lesions. Immunocompromised patients, such as AIDS patients and transplant patients, who become infected with CMV may also suffer from interstitial pneumonia, hepatitis, gastrointestinal disease, retinitis, pancytopenia, fever, and increased graft rejection.

SUMMARY OF THE INVENTION

The invention features a method of inhibiting a viral infection in a patient, which method includes administering to the patient an effective, antiviral amount of cyclomarin-A (formula I).

In one embodiment, the invention features a method of treating infections caused by one or more viruses from the herpesvirus family, such as HSV-1, HSV-2, CMV, and VZV.

Inhibition of viral infection can be demonstrated by one or more of the following: (a) in vivo, reduction or amelioration of clinical symptoms such as fever, headache, pain, itching, inflammation, extent of autoinoculation, and number, size, extent, and duration of lesions; (b) ex vivo, evidence of antiviral action as shown by an appropriate change (whether increase or decrease) of a measured parameter in a serum-, antibody-, viral, cell-, or enzyme-based assay, many of which are known to those skilled in the art. When the antiviral action is a decrease or inhibition of a parameter, preferably the inhibition is at least 25%, and preferably at least 50%, at least 75%, at least 89%, or at least 95% inhibition relative to a control. When the antiviral action is an increase of a parameter, preferably the increase is at least 25%, and preferably at least 50%, at least 75%, at least 95%, at least 120%, or at least 180% increase, or more relative to a control. Parameters measured both in vivo and ex vivo include viral growth rate, viral nucleic acid synthesis, viral shedding, and frequency of viral transmission (vertical and horizontal).

DETAILED DESCRIPTION OF THE INVENTION

In general, the invention features the use of cyclomarin-A, or an analog or derivative thereof, as an antiviral agent. Cyclomarin-A contains L-alanine, L-valine, L-N-methyl-L-leucine and 4 uncommon amino acids 12,O-methylphenyl L-serine, N-methyl-δ-hydroxy leucine, L-2-amino-3,5-dimethyl hex-4-enoic acid, and 1-(1,1-dimethyl-2,3-epoxypropyl) β-hydroxytyptophan (Ala Val Xaa Xaa Xaa Xaa Xaa (SEQ ID NO: 1)). If the viral infection is in a patient, the method of inhibiting viral infection includes administering to the patient a pharmaceutical composition containing cyclomarin-A or analogs and derivatives thereof. A patient is an animal, such as a mammal (e.g., humans, primates, mice, guinea pigs, rabbits, dogs, cats, horses, and cows). The patient may have one or more viral infections, at least one of which is susceptible to cyclomarin-A. The invention also includes a method of inhibiting an ex vivo viral infection, e.g., adding cyclomarin-A to a viral plaque as a positive control, or to whole blood or a blood product such as serum. Cyclomarin-A may also be useful as disinfectant or an infection-resistance agent for contact lenses, or indwelling devices such as a catheter or medical implant.

(I)

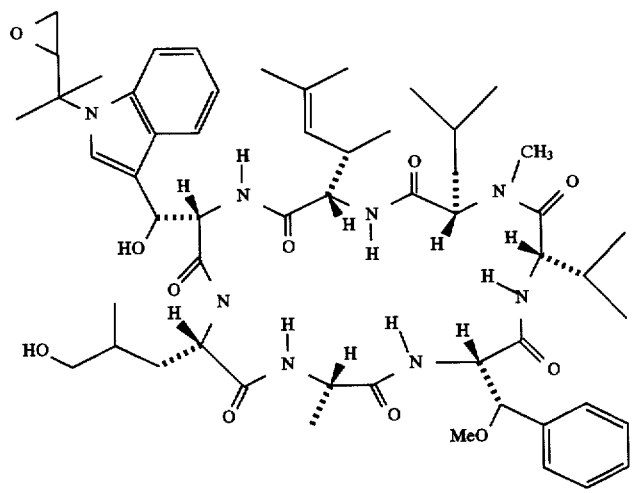

The treatments of the invention are useful for treating infections caused by viral strains which are resistant to other antiviral agents, e.g., nucleoside analogs and their derivatives, including acyclovir, famciclovir, valacyclovir, penciclovir, ganciclovir, and sorivudine. The treatment of the invention can also be used to treat viral infections which are resistant to non-nucleoside antiviral agents, including polymerase inhibitors (e.g., foscarnet), protease inhibitors (e.g., inverase), membrane-active agents which affect, e.g., viral attachment, penetration, or uncoating (e.g., amantadine and rimantadine), antagonists of transcription factors, and the more than 15 anti-CMV antisense agents listed in Table 1, page 1158, in Pari et al., *Antimicrob. Agents Chemother.* 39:1157–1161 (1995), hereby incorporated by reference.

Cyclomarin-A

Exemplary methods of obtaining cyclomarin-A and confirming its structure are described in U.S. Pat. No. 5,444,043 issued on 22 Aug. 1995, which is hereby incorporated by reference; this patent describes the use of cyclomarin-A to treat inflammation. Cyclomarin-A may also be obtained through a combination of organic synthesis, semi-synthesis, and peptide synthesis. In addition to cyclomarin-A, analogs and derivatives thereof may be useful antiviral agents. Derivatives include cyclomarin-A modified by the addition of one or more amino, hydroxyl, or carboxyl protecting groups which are easily cleaved before, during, or after administration. Cleavage includes host or pathogen-induced metabolic cleavage; cleavage caused by physiological conditions (pH, temperature, components present in physiological fluids); or other agents deliberately administered therefor. Subtractive derivatives of cyclomarin-A include antiviral partial amino acid sequences having between 3 and 6 residues, preferably contiguous, of cyclomarin-A. Such partial sequences can be further modified to improve bioavailability (e.g., delivery, absorption), specificity, and activity. Subtractive derivatives may also include appropriate, cleavable protecting groups.

Formulation and Administration

An antiviral composition of the invention can be formulated for administration by injection (e.g., intravenous, intraocular, intraperitoneal, and intramuscular), oral administration (e.g., tablets, capsules, powders, and drops), and topical administration (e.g., tinctures, creams, lotions, gels, sprays, drops, and impregnated bandages). Typical regimens include 0.05%–5% topical eyedrops or eye ointments, 0.01%–5% topical creams, and oral or intravenous formulations for about 5 to about 21 days. The antiviral composition can be administered therapeutically or prophylactically. A disclosed composition contains from about 0.01% to 90% by weight (such as about 0.1% to 20% or about 0.5% to 10%) of cyclomarin-A. For example, a topical semi-solid ointment formulation will contain a concentration of the active ingredient from about 0.1 to 20%, preferably 0.1 to 10% or 0.5 to 5% (e.g., 2%) in a carrier such as a pharmaceutical cream base.

The concentration of active ingredient (cyclomarin-A or derivatives or analogs thereof) in each pharmaceutical formulation and the effective amount of the active compound used to treat a given condition will vary, depending upon the mode of administration, the age and the body weight of the patient, and the condition to be treated. Such amount of the active compound as determined by the attending physician or veterinarian is referred to herein as "effective amount."

In addition to appropriate carriers or excipients, and optional absorption enhancers, the compositions of the invention can also contain one or more additional therapeutic agents, such as anti-inflammatory agents, anti-viral agents, or analgesics. Alternatively, the method of treatment may include separate administration of an additional pharmaceutical composition containing another anti-viral agent (such as acyclovir), or other therapeutic agent. A composition of the invention may also include cyclomarin-A and one or more derivatives or analogs thereof. A composition of the invention may be formulated for various methods of administration, and may further be formulated for controlled release, such as an implant, transdermal patch, or a capsule.

Solid formulations of the compositions for oral administration may contain suitable carriers or diluents such as cyclodextrins, corn starch, gelatin, lactose, acacia, sucrose, microcrystalline cellulose, kaolin, mannitol, dicalcium phosphate, calcium carbonate, sodium chloride, and alginic acid. Disintegrators that can be used include microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as cyclodextrins, methylcellulose, alginates, tragacanth, pectin, kelgin, carrageenan, acacia, polyvinylpyrrolidone, 2-pyrrolidone, and polyvinyl alcohol. The liquid formulations may also include solutions, emulsions, syrups and elixirs containing, together with the active compound(s), wetting agents, sweeteners, and coloring and flavoring agents.

Injectable formulations of the compositions may contain various carriers such as vegetable oils (e.g., sesame oil), dimethylacetamide, dimethylformamide, dimethylsulfoxide, glycerol formal, cyclodextrins, ethyl lactate, ethyl carbonate, isopropyl myristate, ethanol, polyols (glycerol, propylene glycol, liquid polyethylene glycol, polyethylene glycol 400, and the like). For intravenous injections, water soluble versions of the compounds may be administered by the drip method whereby a pharmaceutical formulation containing the antiviral and a physiologically acceptable diluent is infused. Physiologically acceptable diluents may include, for example, 5% dextrose, 0.9% saline, Ringer's solution or other suitable diluents. For intramuscular preparations, a sterile formulation of a suitable soluble salt form of the compounds can be dissolved and administered in a pharmaceutical diluent such as Water-for-Injection, 0.9% saline, or 5% glucose solution. A suitable insoluble form of the compound may be prepared and administered as a suspension (e.g., between 0.5 and 10%) in an aqueous base or a pharmaceutically acceptable oil base, such as an ester of a long chain fatty acid, (e.g. ethyl oleate). In one embodiment, a pharmaceutical composition is administered by intraocular injection or other instillation such as a pump for, e.g., CMV-related ocular conditions.

The following examples are illustrative, not limitative, of the invention.

EXAMPLES

Example 1

HSV-2 ELISA Assay

The ability of cyclomarin-A to inhibit HSV-2 was tested in a culture-based ELISA assay. This assay measures viral glycoprotein inserted into the surface membrane of infected cells, a step in the process of viral replication. Vero cells (African Green monkey kidney cells) were grown in RPMI-1640 medium with L-glutamine (Quality Biological, Gaithersburg, Md.) with 5% fetal bovine serum (FBS) and passaged twice weekly by trypsinization. These were plated in 96-well sterile tissue culture plates at $2 \times 10^4$ cells/well. After incubation overnight at 37° C. in a humidified atmosphere with 5% $CO_2$, wells were inoculated with 1000 plaque forming units per well (PFU/well) HSV-2 (MacIntyre strain, ATCC # VR-539), previously titered by plaque assay and stored at −80° C. Virus was absorbed for 1 hour. Cyclomarin-A was diluted to concentrations between $10^{-7}$ g/ml and $10^{-4}$ g/ml in 50% DMSO and added to the cells in a final volume of 1.5 µl with 150 µl RPMI and 1% FBS. The final DMSO concentration was 0.5%. Plates were incubated for 18 hours at 37° C., and fixed with 10% formalin to inactivate the virus.

An ELISA was performed to assay viral glycoprotein on the cell surface and, hence, viral replication. Plates were incubated for 1 hour with a rabbit anti-HSV-2 IgG antibody diluted 1:5000 (DAKO, Carpenteria, Calif., catalog #B116), washed with PBS and incubated another hour with an HRP-labeled goat anti-rabbit antibody diluted 1:4000 (DAKO, catalog #PO448). After washing with PBS, TMB substrate was added for 15 minutes and reaction was stopped with addition of 1M phosphoric acid. OD was measured spectrophotometrically at a wavelength of 450 nm. Percent inhibition of HSV-2 was calculated against an infected, vehicle control (DMSO) with no drug added. Cyclomarin-A was found to inhibit HSV-2 replicates in this assay with an $IC_{50}$ of 3.01 µg/ml.

Example 2

| Plaque Reduction Assay: Experimental Design | | |
| --- | --- | --- |
| NAME | REPLICATES | DESCRIPTION |
| Cell Control | 3 | Media + Cells |
| Virus Control | 3 | Media + Cells + virus |
| Acyclovir Control | 3 | Media + Cells + virus + Acyclovir (10 µg/ml) |
| Cyclomarin-A | 3 | Media + Cells + virus + Cyclomarin-A concentrations |

Vero cells (ATCC # CCL81) seeded in 24-well plates at 90–100% confluency were used in this study. On the day of infection, the culture media was aspirated from each well. The media in the cell control wells was replaced with 0.2 ml of fresh media whereas that in the virus control and test wells was replaced with 0.2 ml of the viral inoculum (HSV-2 strain VR-734 from ATCC at an input of 50 plaque-forming units (PFU) per well). The plates were incubated for 2 hours at 36°–38° C. in 5–7% $CO_2$.

Following the 2 hour viral adsorption period, the media was removed from the cell control wells and replaced with 1.0 ml of fresh culture media containing various concentrations of cyclomarin-A. Final concentration of DMSO in each dilution was 0.5%. The plates were subsequently incubated at 36°–38° C. and 5–7% $CO_2$ in humidified air until the plaques were well defined.

Two days after infection when primary foci were apparent in the virus control wells, the cells in all wells were fixed with 10% formalin in phosphate buffered saline (PBS), stained with 0.8% Crystal Violet, and air-dried. Plaques were counted with the aid of an inverted microscope. Counts were recorded in triplicate and the data was graphically analyzed to determine the test article concentrations that produced 50% ($IC_{50}$) and 90% ($IC_{90}$) reductions of plaque-forming units. These values were 3.85 µg/ml and 6.03 µg/ml, respectively, for cyclomarin-A.

Example 3

In a plaque-reduction assay similar to that described in Example 2, cyclomarin-A was found to be active against HSV-1 (strain ATCC # VR-733) with an $IC_{50}$ of 3.22 µg/ml and an $IC_{90}$ of 5.47 µg/ml.

Example 4

In a plaque-reduction assay similar to that described in Example 2, cyclomarin-A was found to be active against a thymidine kinase deficient (TK-) acyclovir-resistant clinical isolate of HSV-2 (Viromed, Inc., Minneapolis, Minn.), with an $IC_{50}$ of 1.35 µg/ml and an $IC_{90}$ of 5.38 µg/ml.

Example 5

Multiplicity of Infection (MOI)

The effect of multiplicity of virus infection on cyclomarin-A activity was examined using the HSV-2 ELISA assay described in Example 1. Vero cell cultures were inoculated with HSV-2 to a final concentration of 500, 1000, 2500, and 5000 PFU/well. After cyclomarin-A was added to cells in 150 µl RPMI and 1% FBS, cells were incubated for 18 hours at which time the ELISA assay was completed. Percent inhibition of HSV-2 replication was calculated against an infected, vehicle control (DMSO) at the appropriate MOI with no drug added. The effect of 6.25 µg/ml cyclomarin-A was decreased from 51% inhibition at 500 PFU/well to 40% inhibition at 1000 PFU/well, 17% inhibition at 2,500 PFU/well, and no detectable inhibition at 5000 PFU/well. These data support an anti-viral, rather than anti-cellular, mechanism of action.

Example 6

Combination Study

Cyclomarin-A was also tested in combination with a known inhibitor of HSV-2, acyclovir, using the HSV-2 ELISA assay of Example 1. One and one-half microliters of stock solutions of each compound was added to cells in a final volume of 150 µl RPMI and 1% FBS. Final concentration of cyclomarin-A ranged from 0 to 16 µg/ml; and final concentration of acyclovir ranged from 0 to 5 µg/ml. DMSO concentration for combined drugs, cyclomarin-A and acyclovir, was 0.65%. Cyclomarin-A showed no interference with acyclovir.

Example 7

Vero Cell Growth Inhibition

The effect of cyclomarin-A on the growth of uninfected Vero cells was examined. Vero cells were grown in RPMI with 5% FBS and passaged twice weekly by trypsinization. These were plated in 96 well sterile tissue culture plates at $2 \times 10^4$ cells/well in 200 µl and incubated overnight at 37° C. in a humidified atmosphere with 5% $CO_2$. Cyclomarin-A (10 mg/ml stock solution) was serially diluted (100, 50, 25 and 12.5 µg/ml final concentrations) in 100% DMSO, and added to the cells in a volume of 2 µl. Final DMSO concentration was 1%. Plates were incubated at 37° C. for 48 hours. Cells were fixed by addition of 50% TCA to each well. Plates were incubated at 4° C. for 1 hour. After washing cells with distilled water 0.4% SRB (sulforhodamine B in 1% acetic acid) stain was added to each well. After 25 minutes the stain was washed away with 1% acetic acid and wells were allowed to dry. The remaining stain was resolubilized in 10 mM Tris pH 10.0. Optical density (OD) was determined spectrophotometrically at 650 nm. Percent inhibition of cell growth was calculated based on no drug, vehicle (1% DMSO) control wells as 100%. Concentrations of cyclomarin-A below 50 μg/ml had no effect on cell growth with mild growth inhibition (27–33% inhibition) of Vero cells observed at cyclomarin-A concentration of 100 μg/ml.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

Exposing an animal to a compound encompasses more than administering a compound to an animal. An animal is exposed to a compound when either the compound itself, or a prodrug or metabolic precursor of the compound, is administered to the animal.

Similarly, other embodiments of the invention provide a method of inhibiting a viral infection which includes exposing an animal in need of such exposure to a pharmaceutically effective amount of a metabolite of a compound of formula (I), or a prodrug or metabolic precursor of a metabolite of a compound of formula (I), thereby inhibiting the viral infection in the animal. Clearly, a method of inhibiting a viral infection which includes administering a compound of formula (I) inherently results in exposing the animal to a metabolite of the compound of formula (I).

ing cyclomarin-A (SEQ ID NO: 1), wherein the virus is of the herpesvirus family.

2. The method of claim 1, wherein said virus is selected from Herpes Simplex virus 1, Herpes Simplex virus 2, Cytomegalovirus, Varicella Zoster virus, Epstein-Barr virus, and Human Herpes viruses 6–8.

3. The method of claim 2, wherein said virus is Herpes Simplex virus 1.

4. The method of claim 2, wherein said virus is Herpes Simplex virus 2.

5. The method of claim 2, wherein said virus is Cytomegalovirus.

6. The method of claim 2, wherein said virus is Varicella Zoster virus.

7. The method of claim 1, wherein said virus is of a strain resistant to an antiviral nucleoside analog.

8. The method of claim 2, wherein said virus is of a strain resistant to acyclovir or famciclovir.

9. The method of claim 1, wherein administration is topical.

10. The method of claim 1, wherein administration is systemic.

11. The method of claim 10, wherein administration is by injection.

12. The method of claim 1, wherein said composition comprises a pharmaceutically acceptable carrier, and is formulated for controlled release.

13. The method of claim 12, wherein said composition is formulated as an implant or a transdermal patch.

What is claimed is:

1. A method of inhibiting a viral infection in a patient, said method comprising administering to said patient an effective antiviral amount of a pharmaceutical composition compris- 14. The method of claim 1, wherein administration is intraocular.

* * * * *

UNITED STATES PATENT AND TRADEMARK OFFICE
CERTIFICATE OF CORRECTION

PATENT NO. : 5,759,995            Page 1 of 2
DATED     : June 2, 1998
INVENTOR(S): Christopher J. Pazoles and Scott A. Siegel It is certified that error appears in the above-identified patent and that said Letters Patent is hereby corrected as shown below:

on the title page, item [56],
Under "References Cited", please add the following:

--Other Publications

Clercq, Erik De, Journal of Antimicrobial Chemotherapy, Vol. 32, (1993), Suppl. A, pp. 121-132

Corey, L., Journal of Medical Virology Supplement, Vol. 1, pp. 7-12 (1993)

Ljungman, Per, Annals of Medicine, Vol. 25, Pp. 329-333 (1993)--

And at

Col. 1, lines 39-59, in Formula I, insert "-CH$_3$" where indicated below:

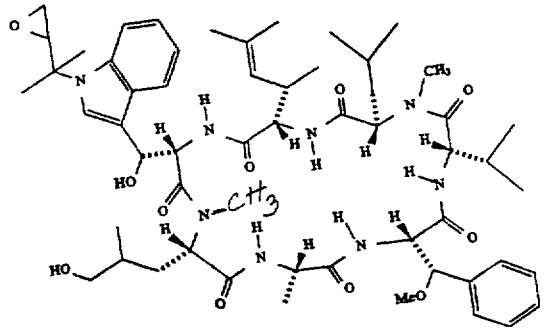

UNITED STATES PATENT AND TRADEMARK OFFICE
CERTIFICATE OF CORRECTION

PATENT NO. : 5,759,995
DATED : June 2, 1998
INVENTOR(S) : Christopher J. Pazoles and Scott A. Siegel It is certified that error appears in the above-identified patent and that said Letters Patent is hereby corrected as shown below:

Col. 7, in the sequence listing, "(B) TYPE: amino acid" should be --(B) TYPE: protein--.

Signed and Sealed this

Second Day of February, 1999

Attest:

Attesting Officer

*Acting Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: circular ( i i ) MOLECULE TYPE: peptide ( i x ) FEATURE: Other: Where first Xaa is L-N-methyl-L-leucine;
        second Xaa is 12,O-methylphenyl L-serine; third Xaa
        is N-methyl- delta-hydroxy leucine; fourth Xaa is
        L-2-amino- 3,5-dimethyl hex-4-enoic acid; and fifth Xaa
        is 1-(1,1- dimethyl-2,3-epoxypropyl) beta-
        hydroxytryptophan ( x i ) SEQUENCE DESCRIPTION: SEQ ID NO:1:

Ala  Val  Xaa  Xaa  Xaa  Xaa  Xaa
1                     5